(12) United States Patent
Keller (10) Patent No.: US 10,492,698 B2
(45) Date of Patent: Dec. 3, 2019

(54) PRESSURE-SENSING INTRAVASCULAR DEVICES, SYSTEMS, AND METHODS WITH WRAPPED PRESSURE-SENSING COMPONENT

(71) Applicant: Volcano Corporation, San Diego, CA (US)

(72) Inventor: Katie Keller, San Diego, CA (US)

(73) Assignee: VOLCANO CORPORATION, San Diego, CA (US)

( * ) Notice: Subject to any disclaimer, the term of this patent is extended or adjusted under 35 U.S.C. 154(b) by 69 days.

(21) Appl. No.: 14/845,039

(22) Filed: Sep. 3, 2015

(65) Prior Publication Data

US 2016/0066802 A1 Mar. 10, 2016

Related U.S. Application Data

(60) Provisional application No. 62/045,996, filed on Sep. 4, 2014.

(51) Int. Cl.
| | |
|---|---|
| *A61B 6/00* | (2006.01) |
| *A61B 5/0215* | (2006.01) |
| *A61B 5/00* | (2006.01) |
| *A61M 25/00* | (2006.01) |
| *A61M 25/01* | (2006.01) |

(52) U.S. Cl.
CPC ........ *A61B 5/02154* (2013.01); *A61B 5/0215* (2013.01); *A61B 5/6851* (2013.01); *A61B 5/6852* (2013.01); *A61B 2560/04* (2013.01); *A61B 2562/0247* (2013.01); *A61M 2025/0002* (2013.01); *A61M 2025/0177* (2013.01); *A61M 2205/0294* (2013.01)

(58) Field of Classification Search
CPC .. A61M 2025/0002; A61M 2025/0177; A61M 2205/0294; A61B 2560/04; A61B 2562/0247; A61B 5/0215; A61B 5/02154; A61B 5/6851; A61B 5/6852
See application file for complete search history.

(56) References Cited

U.S. PATENT DOCUMENTS

| | | | | |
|---|---|---|---|---|
| 4,873,990 | A | * | 10/1989 | Holmes ................. A61B 5/036 600/488 |
| 5,336,184 | A | * | 8/1994 | Teirstein ............. A61M 25/104 604/103.04 |
| 6,546,787 | B1 | * | 4/2003 | Schiller ................ A61B 5/103 73/781 |
| 6,976,965 | B2 | * | 12/2005 | Corl ..................... A61B 5/0215 600/486 |

(Continued)

FOREIGN PATENT DOCUMENTS

| | | |
|---|---|---|
| CN | 103720463 A | 4/2014 |
| WO | 20110161212 A1 | 12/2011 |

*Primary Examiner* — Lindsey G Wehrheim (57) ABSTRACT

Pressure-sensing intravascular devices, systems, and methods are provided. In some instances, the pressure-sensing intravascular devices include a cylindrical body having a proximal portion and a distal portion; a pressure-sensing component coupled to the distal portion of the cylindrical body, the pressure-sensing component being at least partially wrapped around a circumference of the cylindrical body; and a communication cable coupled to the pressure sensing component. The intravascular devices can be catheters and/or guidewire. Associated systems and methods are also provided.

21 Claims, 4 Drawing Sheets

(56) References Cited

U.S. PATENT DOCUMENTS

| | | | |
|---|---|---|---|
| 2004/0068203 A1* | 4/2004 | Gellman | A61B 5/22 600/587 |
| 2005/0187487 A1* | 8/2005 | Azizkhan | A61B 5/0215 600/561 |
| 2009/0004767 A1* | 1/2009 | Parks | G01L 1/146 438/53 |
| 2009/0036779 A1* | 2/2009 | Fukuda | A61B 8/14 600/459 |
| 2010/0241008 A1 | 9/2010 | Belleville et al. | |
| 2010/0298895 A1* | 11/2010 | Ghaffari | A61B 1/00082 607/3 |
| 2013/0131523 A1 | 5/2013 | Suchecki et al. | |
| 2014/0180030 A1 | 6/2014 | Dorando | |

* cited by examiner

PRESSURE-SENSING INTRAVASCULAR DEVICES, SYSTEMS, AND METHODS WITH WRAPPED PRESSURE-SENSING COMPONENT

CROSS REFERENCE TO RELATED APPLICATIONS

The present application claims priority to and the benefit of the U.S. Provisional Patent Application Nos. 62/045,996, filed Sep. 4, 2014, which is hereby incorporated by reference in its entirety.

TECHNICAL FIELD

Embodiments described herein relate to the field of medical devices. More particularly, embodiments described herein are related to the field of intravascular devices with a pressure-sensing component.

BACKGROUND

Cardiovascular diseases pose a serious health risk, often requiring emergency operations to prevent death in patients. One main cause of cardiovascular diseases is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the steno sis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guidewires are utilized to measure the pressure within the blood vessel, visualize the inner lumen of the blood vessel, and/or otherwise obtain data related to the blood vessel. To date, guidewires containing pressure sensors, imaging elements, and/or other electronic, optical, or electro-optical components have suffered from reduced performance characteristics compared to standard guidewires that do not contain such components. For example, the handling performance of previous guidewires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guidewire. Similarly, catheters containing pressure sensors, imaging elements, and/or other electronic, optical, or electro-optical components have suffered from reduced performance characteristics compared to catheters that do not contain such components. For example, the addition of such components in previous catheters has alters the profile of the catheter from a round, streamline cross-section to a larger, asymmetric cross-section. The altered profiles hamper maneuverability in narrow vascular lumen, which can cause damage to the vessels during procedures using such a device. Further, the altered profiles can affect the pressure sensor readings by changing the environment's blood flow near the sensor.

Accordingly, there remains a need for improved intravascular devices and systems that include one or more pressure-sensing components.

SUMMARY

Pressure-sensing intravascular devices, systems, and methods are provided.

In some instances, the pressure-sensing intravascular devices include a cylindrical body having a proximal portion and a distal portion; a pressure-sensing component coupled to the distal portion of the cylindrical body, the pressure-sensing component being at least partially wrapped around a circumference of the cylindrical body; and a communication cable coupled to the pressure sensing component. The intravascular devices can be catheters and/or guidewire.

Associated systems and methods are also provided. For example, in some instances a system includes a pressure-sensing intravascular device that having a cylindrical body having a proximal portion and a distal portion; a pressure-sensing component coupled to the distal portion of the cylindrical body, the pressure-sensing component being at least partially wrapped around a circumference of the cylindrical body; and a communication cable coupled to the pressure sensing component; and a processing system in communication with the pressure-sensing intravascular device.

Additional aspects, features, and advantages of the present disclosure will become apparent from the following detailed description.

DETAILED DESCRIPTION

For the purpose of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1:
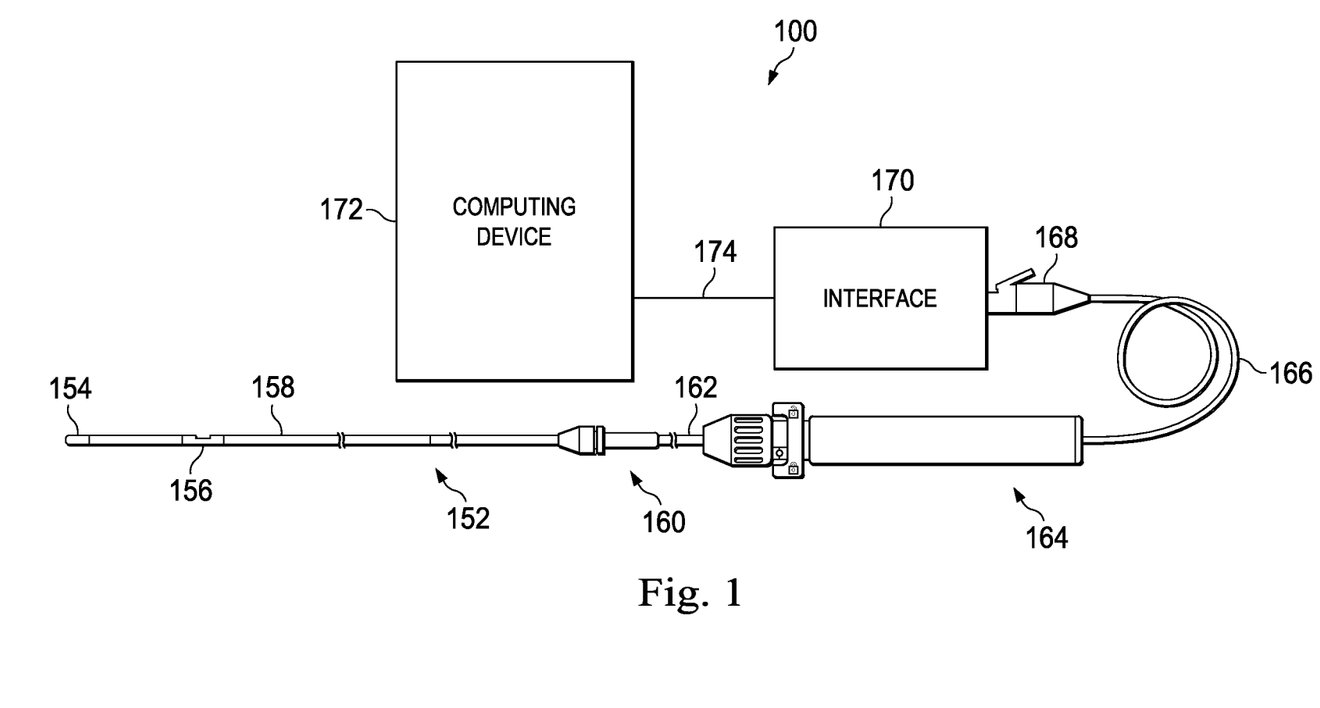
FIG. 1 illustrates a diagrammatic, schematic view of a system according to an embodiment of the present disclosure.

Referring to FIG. 1, shown therein is system 100 according to an embodiment of the present disclosure. In that regard, FIG. 1 is a diagrammatic, schematic view of the system 100. As shown, the system 100 includes an intravascular device 152. In that regard, in some embodiments, intravascular device 152 may include a guide wire. In other embodiments, intravascular device 152 may include a catheter. In the illustrated embodiment, the intravascular device 152 is a guide wire having a proximal portion 162, a distal portion 154, and a pressure sensing portion 156 positioned adjacent the distal portion. In that regard, the pressure sensing portion is spaced approximately 3 cm from a distal tip of the intravascular device 152. In the illustrated embodiment, the pressure sensing portion 156 contains at least a pressure sensor configured to monitor a pressure within a lumen in which the intravascular device 152 is positioned. A shaft 158 extends proximally from the pressure sensing portion 156. A torque device 160 is positioned over and coupled to a connector 164. A cable 166 extends from connector 164 to a connector 168. In some instances, connector 168 is configured to be plugged into an interface 170. In that regard, interface 170 is a patient interface module (PIM) in some instance. In some instances, the cable 166 is replaced with a wireless connection. In that regard, it is understood that various communication pathways between the intravascular device and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis. Accordingly, it is understood that any steps related to data acquisition, data processing, instrument control, and/or processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5 Imaging System or the s5i Imaging System, each available from Volcano Corporation. In some instances, the computing device 172 is portable (e.g., handheld, on a rolling cart, etc.). Further it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the intravascular device 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that connection 174 is wireless in some instances. In some instances, connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

It is understood that one or more components of the system 100 are not included, are implemented in a different arrangement/order, and/or are replaced with an alternative device/mechanism in other embodiments of the present disclosure. For example, in some instances, the system 100 does not include interface 170. In such instances, the connector 168 (or other similar connector in communication with intravascular device 152) may plug into a port associated with computing device 172. Alternatively, the intravascular device 152 may communicate wirelessly with the computing device 172. Generally speaking, the communication pathway between the intravascular device 152 and the computing device 172 may have no intermediate nodes (i.e., a direct connection), one intermediate node between the instrument and the computing device, or a plurality of intermediate nodes between the instrument and the computing device.

Figure 2:
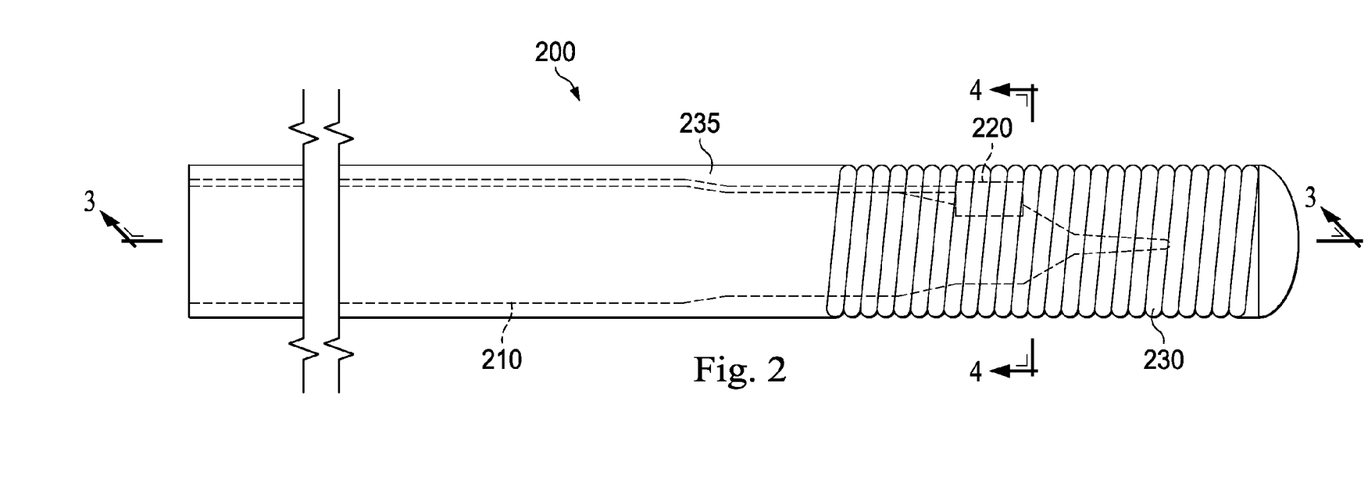
FIG. 2 illustrates a partial view of an intravascular device according to an embodiment of the present disclosure.
Figure 3:
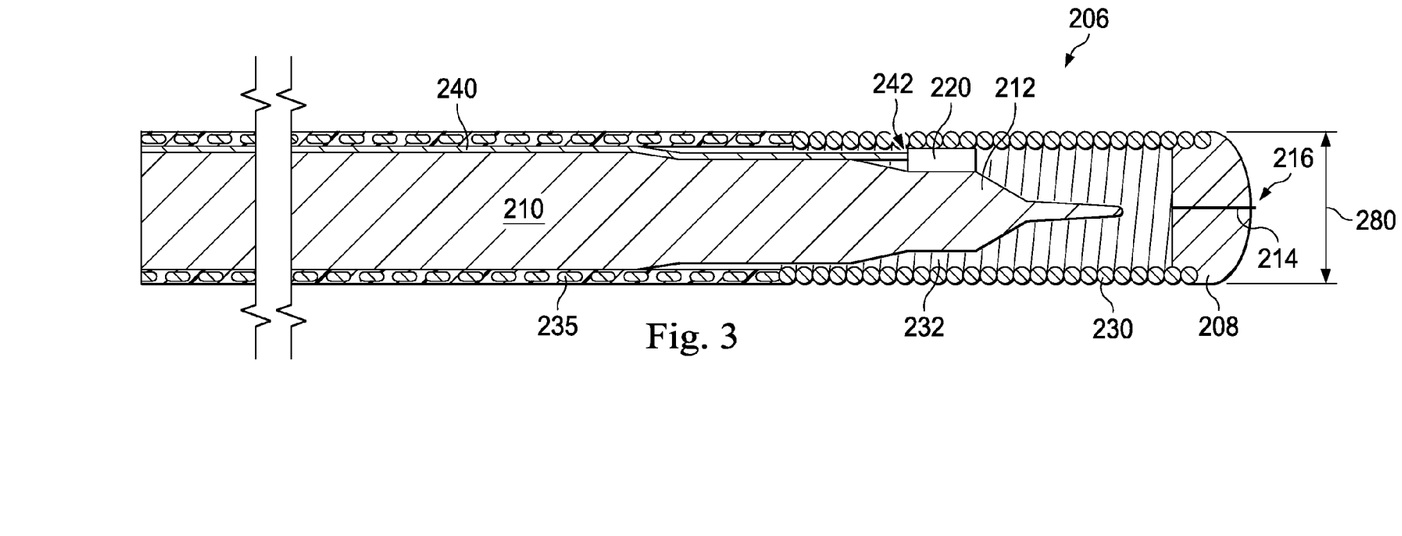
FIG. 3 illustrates an axial cross-section view of a portion of the intravascular device of FIG. 2 taken along section line 3-3 of FIG. 2.
Figure 4:
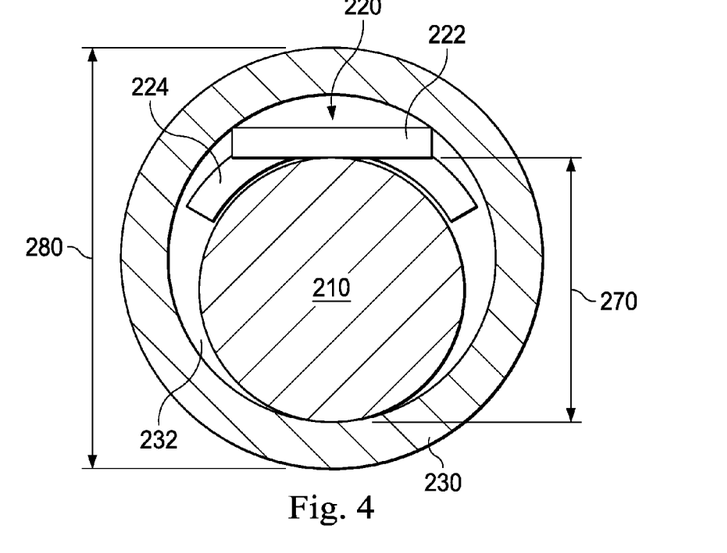
FIG. 4 illustrates a longitudinal cross-section view of a portion of the intravascular device of FIG. 2 taken along section line 4-4 of FIG. 2.

Referring now to FIGS. 2-4, shown therein is a plurality of views of an embodiment of the present disclosure of an intravascular device. FIG. 2 illustrates a partial view of an intravascular device 200 according to embodiments disclosed herein. FIG. 3 illustrates an axial cross-section view of a portion of the intravascular device 200 taken along section line 3-3 of FIG. 2. FIG. 4 illustrates a longitudinal cross-section view of a portion of the intravascular device 200 taken along section line 4-4 of FIG. 2.

Referring more particularly to FIG. 2, shown therein is a portion of an intravascular device 200 according to an embodiment of the present disclosure. As illustrated, the intravascular device 200 is a guide wire. In the illustrated embodiment, the intravascular device 200 includes a core 210 and a pressure-sensing component 220. In that regard, the core 210 and pressure-sensing device 220 are disposed within a flexible element 230 and/or a flexible element 235. In that regard, in some instances the flexible element 230 is a coil spring. In some instances, the flexible element 235 is ribbon coil covered with a polymer coating. For example, in one embodiment the flexible element 335 is a stainless steel ribbon wire coil coated with polyethylene terephthalate (PET). In another embodiment, the flexible element is a polyimide tubing that has a ribbon wire coil embedded therein. For example, in some instances a polyimide or Pebax tubing with embedded coil is utilized for flexible element 235. In some particular embodiments, the ribbon wire coil is embedded within the polyimide tubing.

Referring now to FIG. 3, shown therein is a cross-section of the intravascular device 200 taken along section line 3-3 of FIG. 2. As shown, the intravascular device 200 also includes a distal portion 206 that is configured to be inserted into the patient, including within human vasculature. In that regard, the distal portion 206 has an outer diameter 280 between about 0.0007" (0.0178 mm) and about 0.118" (3.0 mm) in some embodiments, with some particular embodiments having an outer diameter of approximately 0.014" (0.3556 mm) or approximately 0.018" (0.4572 mm)). In the illustrated embodiment of FIG. 3, the intravascular device 200 has an outer diameter 280 of 0.014" (0.3556 mm).

In the illustrated embodiment in FIG. 3, the distal portion 206 of the intravascular device 200 has a distal tip 216 defined by an element 208. In the illustrated embodiment, the distal tip 216 has a rounded profile. In some instances, the element 208 is radiopaque such that the distal tip 216 is identifiable under x-ray, fluoroscopy, and/or other imaging modalities when positioned within a patient. In some particular instances, the element 208 is solder secured to a flexible element 230 and/or a flattened tip core 214. In that regard, in some instances the flexible element 230 is a coil spring. The flattened tip core 214 extends from a distal core 212 towards the distal tip 216. As shown, the distal core 212 tapers to a narrow profile as it extends towards the distal tip 216. In some instances, the distal core 212 is formed of a stainless steel that has been ground down have the desired tapered profile. In some particular instances, the distal core 212 is formed of high tensile strength 304V stainless steel. In an alternative embodiment, the distal core 212 is formed by wrapping a stainless steel shaping ribbon around a nitinol core.

As shown, a pressure-sensing component 220 is disposed around a portion of the core 210. In some embodiments, the pressure-sensing component is fixed to a portion of the core 210 with an adhesive or suitable connection. In some embodiments, the pressure-sensing component 220 is one or more of an electronic component, an optical component, and/or electro-optical component. For example, without limitation, the pressure-sensing component 220 may comprise of one or more of the following types of components: an optical pressure sensor, a piezo-resistive pressure sensor, a fluid column pressure sensor, a temperature sensor, an imaging element, an optical fiber, an ultrasound transducer, a reflector, a mirror, a prism, an ablation element, an RF electrode, a conductor, and/or combinations thereof.

A communication cable 240 extends along the length of the intravascular device 200 from a proximal portion to the distal portion 206. In that regard, the distal end of the communication cable 240 is coupled to the pressure-sensing component 220 at junction 242. The type of communication cable utilized is dependent on the type of electronic, optical, and/or electro-optical components that make up the pressure-sensing component 220. In that regard, the communication cable 240 may include one or more of an electrical conductor, an optical fiber, and/or combinations thereof. Alternatively, the communication cable 240 may be replaced by and/or include a lumen in the case of a fluid column pressure sensor. Appropriate connections are utilized at the junction 242 based on the type of communication lines included within communication cable 240. For example, electrical connections are soldered in some instances, while optical connections pass through an optical connector in some instances.

Adjacent to the core 210 is a space 232. In some embodiments the space includes adhesive. In that regard, the adhesive in the space 232 is utilized to secure at least a portion of the core 210 to the flexible element 230 and/or flexible element 235. In some embodiments, the space 232 wraps completely around the core 210. In alternative embodiments, as illustrated in FIG. 4, the space 232 only partially surrounds the core 210.

Referring more particularly to FIG. 4, shown therein is a cross-section of the intravascular device 200 taken along section line 4-4 of FIG. 2. As shown, the pressure-sensing component 220 is disposed around the core 210. In that regard, the pressure-sensing component 220 is at least partially wrapped around the circumference of the intravascular device 200. In some instances, the pressure-sensing component 220 extends around at least 10%, at least 20%, at least 30%, at least 40%, at least 50%, at least 60%, or at least 70% of the circumference of the intravascular device 200. In some implementations, the pressure-sensing component 220 extends around between about 30% and 50% of the circumference of the intravascular device 200. In some embodiments, the pressure-sensing component 220 includes a pressure sensing portion 222 and a substrate 224. As illustrated, the substrate 224 is wrapped around the core 210. In some embodiments, the substrate 224 is a flexible circuit to which the pressure sensing portion 222 is electrically, optically, and/or mechanically coupled. In that regard, the substrate 224 is at least a portion of a pressure sensor in some instances. In that regard, the substrate 224 is a portion of a piezo-resistive pressure sensor or a fiber optic sensor in some instances. In some embodiments, the substrate 224 is coupled to the pressure sensing portion 222.

As illustrated, the pressure-sensing component 220 includes a pressure sensing portion 222. In some embodiments, the pressure sensing portion 222 is at least a portion of a piezo-resistive pressure sensor. In that regard, the pressure sensing portion 222 may include a diaphragm in some instances. In some embodiments, the pressure sensing portion 222 is at least a portion of a fiber optic sensor. In that regard, the pressure sensing portion 222 may include a portion of diaphragm coupled to at least one optic fiber.

As shown, the portion of the core 210 around which the pressure sensing component 220 is disposed has a diameter 270 smaller than the outer diameter 280 defined by the outer boundaries of the flexible element 230. In the illustrated embodiment, the substrate 224 is wrapped around the portion of the core 210. In that regard, the pressure-sensing component 220 takes up less space in the radial direction between the core 210 and the flexible element 230. In such instances, the diameter 270 can be enlarged relative to the diameter 280 to improve characteristics of the core 210. For example, a larger diameter 270 of the core 210 can improve the handling of the guidewire, easing the process of placing the intravascular device inside the proper lumen in the human body and preventing damage to vascular tissue during the process.

Figure 5:
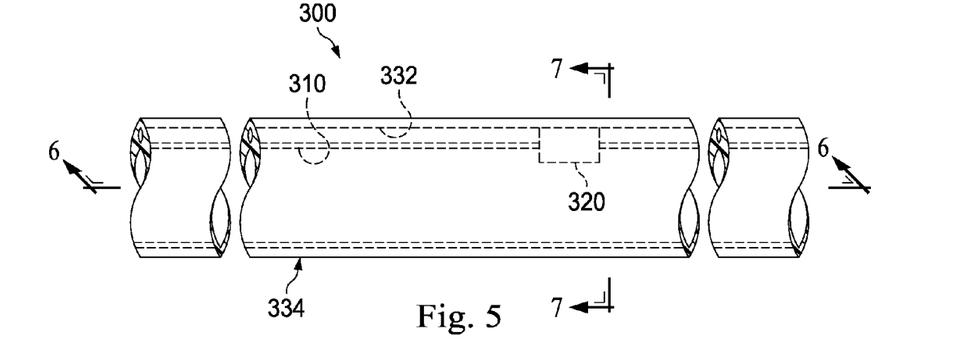
FIG. 5 illustrates a partial view of an intravascular device according to another embodiment of the present disclosure.
Figure 6:
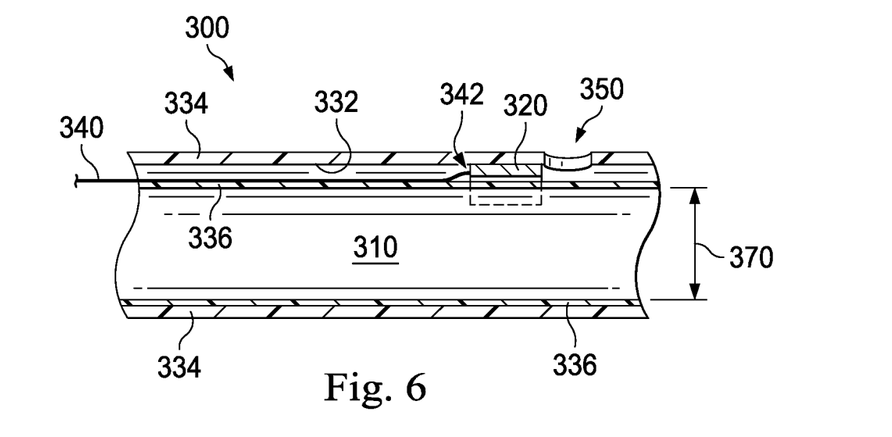
FIG. 6 illustrates an axial cross-section view of a portion of the intravascular device of FIG. 5 taken along section line 6-6 of FIG. 5.
Figure 7:
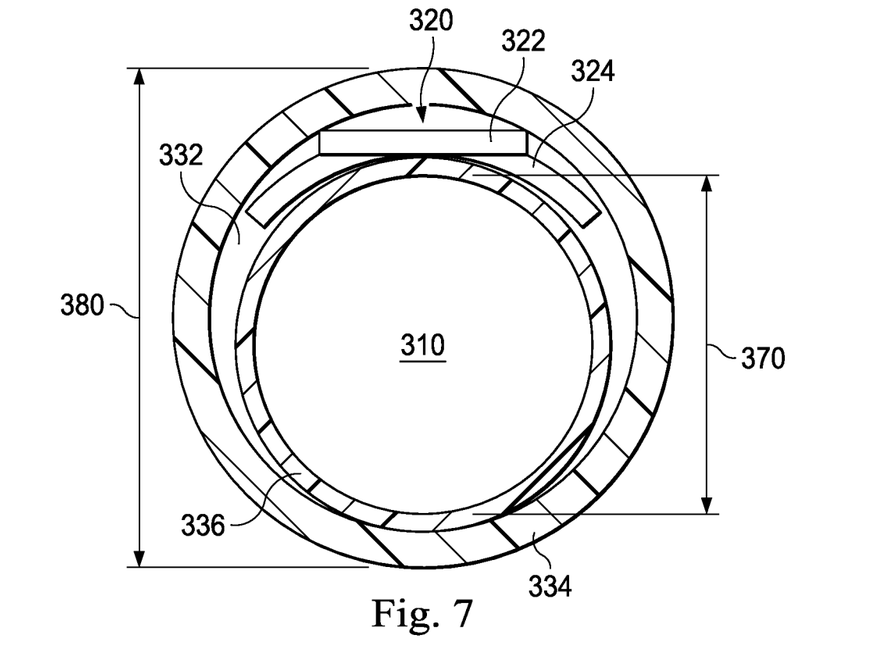
FIG. 7 illustrates a longitudinal cross-section view of a portion of the intravascular device of FIG. 5 taken along section line 7-7 of FIG. 5.

Referring now to FIGS. 5-7, shown therein is a plurality of views of an embodiment of the present disclosure of an intravascular device. FIG. 5 illustrates a partial view of an intravascular device 300 according to embodiments disclosed herein. FIG. 6 illustrates an axial cross-section view of a portion of the intravascular device 300 taken along section line 6-6 of FIG. 5. FIG. 7 illustrates a longitudinal cross-section view of a portion of the intravascular device 300 taken along section line 7-7 of FIG. 5.

Referring more particularly to FIG. 5, shown therein is a part of an intravascular device 300 according to an embodiment of the present disclosure. In the illustrated embodiment, the intravascular device 300 is a catheter. As shown, the intravascular device 300 includes a pressure-sensing component 320 disposed around a guidewire lumen 310, both disposed within a catheter body 334. In that regard, the catheter body 334 can be composed of any material or combination of materials known by persons having ordinary skill in the art.

As shown, the intravascular device 300 includes a space 332 between the guidewire lumen 310 and the catheter body 334. In some embodiments, the guidewire lumen 310 and space 332 are defined by a separate tubular member, as shown in FIGS. 6 and 7. In alternative embodiments, the guidewire lumen 310 and the space 332 are defined by removing interior portions of a singular tubular member. In some instances the space 332 completely surrounds the guidewire lumen 310. In other embodiments the space 332 only partially surrounds the guidewire lumen 310. The space 332 can include a substance in some instances. In that regard, the substance in the space 332 can be an adhesive to fix together any combination of the guidewire lumen 310, pressure-sensing component 320, and the catheter body 334, in some instances.

Referring now to FIG. 6, shown therein is a cross-section of the intravascular device 300 taken along section line 6-6 of FIG. 5. As shown, the intravascular device 300 has an outer diameter 380 which is configured so that a portion of the intravascular device 300 can be inserted into the patient, including within human vasculature. In that regard, the portion of the intravascular device 300 including the pressure-sensing component 320 has an outer diameter 280 between about 0.0007" (0.0178 mm) and about 0.118" (3.0 mm) in some embodiments.

As illustrated, the guidewire lumen 310 is defined by a separate tubular member 336. In some embodiments the intravascular device 300 is configured with a rapid exchange guidewire port. In other embodiments, the intravascular device 300 is configured with an over-the-wire platform. The guidewire lumen 310 has diameter 370. In some embodiments the diameter 370 is between about 0.0007" (0.0178 mm) and about 0.118" (3.0 mm) with some particular embodiments the diameter 370 is approximately 0.014" (0.3556 mm) or approximately 0.018" (0.4572 mm)).

As shown, the intravascular device 300 includes an opening 350 in the catheter body 334. In some instances, the opening 350 is configured to allow a fluid to enter inside of the catheter body 334. In that regard, the fluid interacts with the pressure-sensing component 320. In some particular instances, the fluid is blood and the pressure-sensing component 320 is a pressure sensor. In some embodiments, the opening 350 includes a membrane that prevents solids from entering the catheter body 334 while still allowing fluid to interact with the pressure-sensing component 320. For example, without limitation, the membrane may allow blood to interact enter part of the catheter body 334, but prevent vascular tissue from entering and interfering with the pressure-sensing component 320.

In the illustrated embodiment in FIG. 6, a communication cable 340 extends along the length of the intravascular device 300 from a proximal portion to a distal portion. In that regard, the distal end of the communication cable 340 is coupled to the pressure-sensing component 320 at junction 342. The type of communication cable utilized is dependent on the type of electronic, optical, and/or electro-optical components that make up the pressure-sensing component 320. In that regard, the communication cable 340 may include one or more of an electrical conductor, an optical fiber, and/or combinations thereof. Appropriate connections are utilized at the junction 342 based on the type of communication lines included within communication cable 340. For example, electrical connections are soldered in some instances, while optical connections pass through an optical connector in some instances.

Referring now to FIG. 7, shown therein is a cross-section of the intravascular device 300 taken along section line 7-7 of FIG. 5. As shown, the pressure-sensing component 320 is disposed around a guidewire lumen 310 which has a diameter 370. In that regard, the pressure-sensing component 320 is at least partially wrapped around the circumference of the intravascular device 300. In some instances, the pressure-sensing component 320 extends around at least 10%, at least 20%, at least 30%, at least 40%, at least 50%, at least 60%, or at least 70% of the circumference of the intravascular device 300. In some implementations, the pressure-sensing component 320 extends around between about 30% and 50% of the circumference of the intravascular device 300. In some embodiments, the pressure-sensing component 320 includes a pressure sensing portion 322 and a substrate 324. In particular instances, as illustrated, the substrate 324 is wrapped around the guidewire lumen 310. In some embodiments, the substrate 324 is a flexible circuit. In that regard, the substrate 324 is at least a portion of a pressure sensor in some instances. In particular instances, the substrate 324 is at least a portion of a pressure sensor. In that regard, the substrate 324 is a portion of a piezo-resistive pressure sensor or a fiber optic sensor in some instances. In some embodiments, the substrate 324 is coupled to the pressure sensing portion 322.

As illustrated, the pressure-sensing component 320 includes a pressure sensing portion 322. In some embodiments, the pressure sensing portion 322 is at least a portion of a piezo-resistive pressure sensor. In that regard, the pressure sensing portion 322 may include a diaphragm in some instances. In alternative embodiments, the pressure sensing portion 322 is at least a portion of a fiber optic sensor. In that regard, the pressure sensing portion 322 may include a portion of diaphragm coupled to at least one optic fiber.

As shown, the guidewire lumen 310 around which the pressure sensing component 320 is disposed has a diameter 370 which is smaller than the outer diameter 380 of the catheter body 334. In the illustrated embodiment, the substrate 324 is wrapped around the portion of the guidewire lumen 310. In that regard, the pressure-sensing component 320 takes up less space in the radial direction between the guidewire lumen 310 and the catheter body 334. In such instances, the diameter 370 can be enlarged relative to the outer diameter 380 to improve characteristics of the guidewire lumen 310. For example, a larger diameter 370 can incorporate a larger guidewire. By wrapping the pressure-sensing component 320 around the guidewire lumen 310, the illustrated embodiment demonstrates a smoother and rounder profile of the catheter body 334 adjacent the pressure-sensing component 320, enabling easier access to vascular lumen and preventing inadvertent damage while navigating the intravascular device 300 inside of the human body. Additionally, the outer diameter 380 of the catheter body 334 can be reduced while maintaining the same diameter 370 of the guidewire lumen 310 with the obvious effect of being less intrusive while inside human lumen.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A pressure-sensing intravascular device, comprising:
a cylindrical body having a proximal portion and a distal portion;
a pressure-sensing component coupled to the distal portion of the cylindrical body, the pressure-sensing component including a pressure-sensing portion and a substrate coupled to the pressure-sensing portion, wherein the pressure-sensing portion extends in planar manner such that the pressure-sensing portion does not curve around a circumference of the cylindrical body, wherein opposites sides of the substrate are wider than the pressure-sensing portion and wrap around at least a portion of the circumference of the cylindrical body, wherein at least a portion of an outer layer of the pressure-sensing intravascular device surrounds the opposite sides of the substrate wrapped around the at least the portion of the circumference of the cylindrical body; and
a communication cable coupled to the pressure-sensing component.

2. The pressure-sensing intravascular device of claim 1, wherein the cylindrical body is a tubular member defining an internal lumen, the tubular member extending longitudinally within a catheter body.

3. The pressure-sensing intravascular device of claim 2, wherein the internal lumen is sized to receive a guidewire having a diameter of at least one of 0.014" or 0.018".

4. The pressure-sensing intravascular device of claim 2, wherein the catheter body includes a rapid-exchange port in communication with the internal lumen.

5. The pressure-sensing intravascular device of claim 2, wherein the pressure-sensing component extends around at least 30% of the circumference of the cylindrical body.

6. The pressure-sensing intravascular device of claim 2, wherein the pressure-sensing component extends around at least 50% of the circumference of the cylindrical body.

7. The pressure-sensing intravascular device of claim 2, wherein the pressure-sensing component is disposed between an inner surface of the catheter body and an outer surface of the tubular member.

8. The pressure-sensing intravascular device of claim 1, wherein the cylindrical body is a core wire extending longitudinally within a flexible element of a guidewire.

9. The pressure-sensing intravascular device of claim 8, wherein the guidewire has an outer diameter of at least one of approximately 0.014", approximately 0.018", or approximately 0.035".

10. The pressure-sensing intravascular device of claim 8, wherein the pressure-sensing component extends around at least 30% of the circumference of the cylindrical body.

11. The pressure-sensing intravascular device of claim 8, wherein the pressure-sensing component extends around at least 50% of the circumference of the cylindrical body.

12. The pressure-sensing intravascular device of claim 8, wherein the pressure-sensing component is disposed between an inner surface of the flexible element and an outer surface of the core wire.

13. The pressure-sensing intravascular device of claim 1, wherein the pressure-sensing component comprises a fiber-optic pressure sensor.

14. The pressure-sensing intravascular device of claim 1, wherein the pressure-sensing component comprises a piezo-resistive pressure sensor.

15. The pressure-sensing intravascular device of claim 1, wherein the pressure-sensing component is positioned over the distal portion of the cylindrical body.

16. A system, comprising:
a pressure-sensing intravascular device that includes:
a cylindrical body having a proximal portion and a distal portion;
a pressure-sensing component positioned over the distal portion of the cylindrical body, the pressure-sensing component including a pressure-sensing portion and a substrate coupled to the pressure-sensing portion, wherein the substrate is wrapped around at least a portion of a circumference of the cylindrical body and the pressure-sensing portion extends in a planar manner such that the pressure-sensing portion does not curve around the circumference of the cylindrical body, wherein opposites sides of the substrate are wider than the pressure-sensing portion, wherein at least a portion of an outer layer of the pressure-sensing intravascular device surrounds the opposite sides of the substrate wrapped around at least the portion of the circumference of the cylindrical body; and
a communication cable coupled to the pressure-sensing component; and a processing system in communication with the pressure-sensing intravascular device.

17. The system of claim 16, further comprising a display in communication with the processing system.

18. The system of claim 16, wherein the pressure-sensing intravascular device is a catheter and the cylindrical body is a tubular member defining an internal lumen, the tubular member extending longitudinally within a catheter body of the catheter.

19. The system of claim 16, wherein the pressure-sensing intravascular device is a guidewire, wherein the guidewire includes a core wire extending longitudinally within a flexible element, and wherein the cylindrical body is the core wire.

20. The system of claim 16, wherein the pressure-sensing component extends around at least 30% of the circumference of the cylindrical body.

21. The system of claim 16, wherein the pressure-sensing component extends around at least 50% of the circumference of the cylindrical body.

\* \* \* \* \*